(12) United States Patent
Saimoto et al.

(10) Patent No.: US 7,622,598 B2
(45) Date of Patent: Nov. 24, 2009

(54) PHENOL DERIVATIVES AND ANTITRYPANOSOMA PREVENTIVE/THERAPEUTIC AGENT COMPRISING THE SAME AS ACTIVE INGREDIENT

(75) Inventors: Hiroyuki Saimoto, Tottori (JP); Yoshihiro Shigemasa, Tottori (JP); Kiyoshi Kita, Tokyo (JP); Yoshisada Yabu, Nagoya (JP); Tomoyoshi Hosokawa, Tokyo (JP); Masaichi Yamamoto, Tokyo (JP)

(73) Assignee: aRigen Pharmaceuticals, Inc., Tokyo (JP)

( * ) Notice: Subject to any disclaimer, the term of this patent is extended or adjusted under 35 U.S.C. 154(b) by 0 days.

(21) Appl. No.: 10/575,653

(22) PCT Filed: Oct. 18, 2004

(86) PCT No.: PCT/JP2004/015390

§ 371 (c)(1),
(2), (4) Date: Dec. 13, 2006

(87) PCT Pub. No.: WO2005/037760

PCT Pub. Date: Apr. 28, 2005

(65) Prior Publication Data

US 2007/0208078 A1    Sep. 6, 2007

(30) Foreign Application Priority Data

Oct. 17, 2003 (WO) .............. PCT/JP03/13310

(51) Int. Cl.
*C07D 307/02* (2006.01)
(52) U.S. Cl. .............. 549/475; 549/476; 549/478
(58) Field of Classification Search .......... 549/475, 549/476, 478
See application file for complete search history.

(56) References Cited

U.S. PATENT DOCUMENTS 3,546,073 A    12/1970    Evans Jr. et al.

FOREIGN PATENT DOCUMENTS

| JP | 9-165332 A | 6/1997 |
| JP | 09165332 | * 6/1997 |
| WO | WO 9404520 | * 3/1994 |

OTHER PUBLICATIONS

J. Med. Chem. 2003, 46, 4113-4123 "Ascochlorin Derivatives as Ligands for Nuclear Hormone Receptors".
Togashi et al., "Ascochlorin Derivatives as Ligands for Nuclear Hormone Receptors", Journal of Medicinal Chemistry, 46(19), 4113-4123 CODEN:JMCMAR; ISSN 0022-2623, 2003, XP002397667, pp. 4113-4123.

* cited by examiner

Primary Examiner—D. Margaret Seaman
Assistant Examiner—Nizal S Chandrakumar
(74) Attorney, Agent, or Firm—Harness, Dickey & Pierce, P.L.C.

(57) ABSTRACT

A compound represented by formula (I):

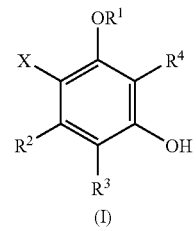

[Formula 1]

(I)

[wherein, for example,
X is a hydrogen atom or a halogen atom;
$R^1$ is a hydrogen atom;
$R^2$ is a hydrogen atom or a $C_{1-4}$ alkyl group;
$R^3$ is —CHO or —COOH; and
$R^4$ is —CH=CH—$(CH_2)_p$—$CH_3$ (wherein p is an integer of 1 to 12), —CH(OH)—$(CH_2)_q$—$CH_3$ (wherein q is an integer of 1 to 13), —CH(OH)—$CH_2$—CH($CH_3$)—$(CH_2)_2$—CH=C($CH_3$)$_2$, —CH=CH—CH($CH_3$)—$(CH_2)_3$—CH($CH_3$)$_2$, —$(CH_2)_2$—CH($CH_3$)—$(CH_2)_3$—CH($CH_3$)$_2$ or —$(CH_2)_8$—$CH_3$], an optical isomer thereof and a pharmaceutically acceptable salt thereof. These compounds have antitrypanosoma activity, and accordingly are useful as drugs for preventing or treating the diseases caused by trypanosoma.

15 Claims, No Drawings

PHENOL DERIVATIVES AND ANTITRYPANOSOMA PREVENTIVE/THERAPEUTIC AGENT COMPRISING THE SAME AS ACTIVE INGREDIENT

TECHNICAL FIELD

The present invention relates to a novel halogen-containing phenol derivative having an alkyl side chain, an antitrypanosoma preventing/treating pharmaceutical composition having the same as an active ingredient, use of these components in producing a pharmaceutical composition for preventing or treating trypanosomiasis and a method of preventing or treating the diseases caused by Trypanosoma.

BACKGROUND ART

Onset of trypanosomiasis is caused by Trypanosoma protozoa and it is said that every year 200,000 to 300,000 of new patients of African sleeping sickness fall sick. At present the number of patients of African sleeping sickness cannot be confirmed due to the low reliability of the investigative data. According to the WHO, at least 150,000 people died of African sleeping sickness in 1996 and it is said that its aftereffect remains in not less than 100,000 people. Beyond that, enormous is the damage to domestic animals caused by a disease called as nagana, and several hundred thousands of cattle which are to be protein sources for people die every year. Further, in the area of about 10,000,000 $km^2$ of savanna equal to the United States of America, cattle-breeding is impossible due to Trypanosoma. Thus, African sleeping sickness remarkably damages the health and the economical development of African people, and this is the reason why the WHO adopts the trypanosomiasis as one of the infectious diseases that should be controlled.

African sleeping sickness is a protozoal infectious disease by,Trypanosoma transmitted through tsetse flies and the protozoa appear in the blood stream in about 10 days after infection. In the initial period of infection the protozoa multiply in the blood stream and give fever, physical weakness, headache, a pain of muscles and joints and a feeling of itching to proceed. On entering the chromic period, the central nerve is affected to show symptoms such as mental confusion and systemic convulsion, and finally the patients lapse into lethargy and are led to death.

The trypanosomiasis of domestic animals has Trypanosoma brucei brucei, Trypanosoma evansi, Trypanosoma congolense and Trypanosoma vivax as pathogens and is a communicable disease which affects domestic animals such as horses, cattle, pigs and dogs and, in addition, mice, guinea pigs, rabbits and the like. Particularly, the loss of cattle and horses is greatest and almost fetal, and they are led to anemia, edema, weakening and the like and fall dead in one month after infection.

In treating trypanosomiasis, pentamidine, melarsoprol, eflornithine and the like are used and there was a feeling in the 1960s that its eradication might be possible. However, these drugs are old and are gradually losing their efficacy. Particularly, the resistance to melarsoprol of an arsenic agent causes a big problem and the situation is so dire that patients with no efficacy only await death and the development of novel antitrypanosoma agents are strongly desired.

Trypanosoma mainly lives in the blood stream of the human body. This bloodstream energy metabolism depends on the glycolytic pathway localized in the organelle characteristic of the protozoa which is called as glycosome and the so-called oxidative phosphorylation does not function. However, in order to efficiently drive this glycolytic pathway, the produced NADH has to be reoxidized, and the glycerol-3-phosphate oxidation system of mitochondria plays an important role in this reoxidation. The terminal oxidase of this oxidation system functions as a quinol oxidase having a reduced ubiquinone as an electron donor and has properties greatly different from those of cytochrome oxidase of an aerobic respiration system which the host has. Particularly, a remarkable point is that the terminal oxidase of the oxidation system is non-sensitive to the cyanide which quickly inhibits the cytochrome oxidase of the host. Then, many researchers centered around Western countries have tried to develop drugs targeting this cyanide resistant oxidase but effective drugs having a selective toxicity have not been obtained.

Under these circumstances the present inventors et al. found that isoprenoid based physiologically active substances of ascochlorin, ascofuranone and derivatives thereof, particularly ascofuranone specifically inhibits the glycerol-3-phosphate oxidation system of trypanosome at a very low concentration of the order of nM and filed a patent application (Japanese Patent Publication A No.: H09-165332). They also clarified that acofuranone exhibits a very strong multiplication inhibition effect in the copresence of glycerin (Molecular and Biochemical Parasitology, 81: 127-136, 1996).

In consideration of practical use of ascofuranone, it was found essential to discover agents which replace glycerin and exhibit an effect of the combined use in a small amount, and by using an alkaloid compound having an indole skeleton existing in a plant of the family Simaroubaceae together with ascofuranone, the prolongation of life and recovery effect in African seeping sickness was found and a patent application was filed (Japanese Patent Application No.: 2003-24643, Japanese Patent Publication A No.: 2004-23601).

DISCLOSURE OF THE INVENTION

PROBLEM TO BE SOLVED BY THE INVENTION

The object of the present invention is to provide an antitrypanosoma treating agent which is effective at a lower concentration than ascofuranone and has high safety.

Means to Solve the Problem

The present inventors have made investigations of antitrypanosoma agents which are effective at a lower concentration than ascofuranone and have high safety and found a strong activity in novel halogen-containing phenol derivatives having an alkyl side chain and a ascofuranoen derivative of some type and completed the present invention.

The present invention provides a compound represented by formula (I),

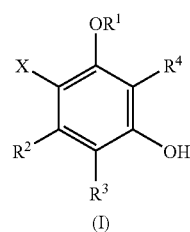

[Formula 1]

(I)

[wherein

X is a hydrogen atom or a halogen atom;

$R^1$ is a hydrogen atom or —$(C_nH_{2n})$—R' (wherein n is an integer of 1 to 5; and R' is a hydrogen atom, a group COOR" or —COR'" of a substituent on any one of the n carbon atoms, wherein R" is a hydrogen atom or a $C_{1-4}$ alkyl group; and R'" is a pyridyl group, an amino group substituted with a $C_{1-4}$ alkyl group, a phenoxyalkyl group having a halogen atom on the carbon atoms of the benzene ring or a phenyl group having a $C_{1-4}$ alkoxy group or a $C_{1-4}$ alkoxycarbonyl group on the carbon atoms of the benzene ring);

$R^2$ is a hydrogen atom or a $C_{1-7}$ alkyl group;

$R^3$ is —CHO or —COOH; and $R^4$ is —CH=CH—$(CH_2)_p$—$CH_3$ (wherein p is an integer of 1 to 12), —CH(OH)—$(CH_2)_q$—$CH_3$ (wherein q is an integer of 1 to 13), —CH(OH)—$CH_2$—$CH(CH_3)$—$(CH_2)_2$—CH=$C(CH_3)_2$, —CH=CH—$CH(CH_3)$—$(CH_2)_3$—CH$(CH_3)_2$, —$(CH_2)_2$—$CH(CH_3)$—$(CH_2)_3$—$CH(CH_3)_2$ or —$(CH_2)_8$—$CH_3$], a compound represented by the following formulae:

[Formula 2-1]

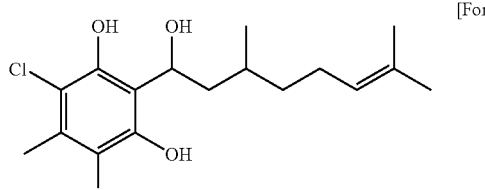

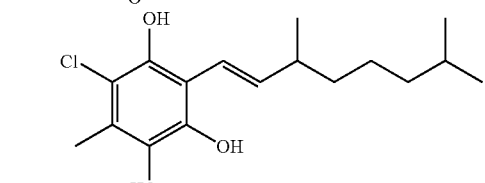

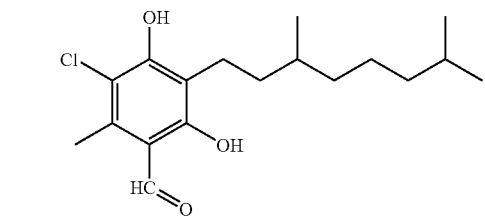

[Formula 2-2]

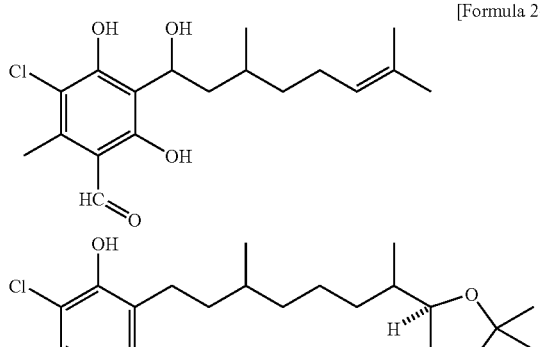

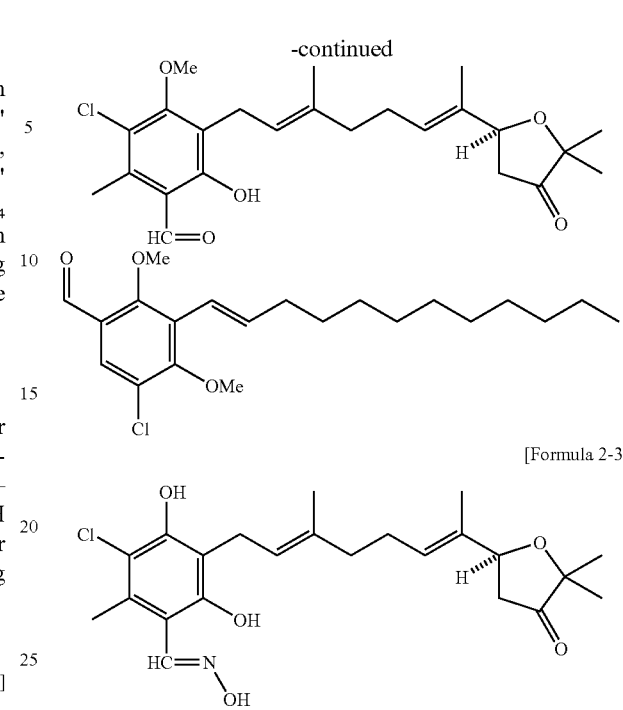

[Formula 2-3]

and an optical isomer thereof and a pharmaceutically acceptable salt thereof.

Further, the present invention provides a pharmaceutical composition comprising at least one of a compound represented by the above described formula (I), an optical isomer thereof and a pharmaceutically acceptable salt thereof, and a pharmaceutically acceptable carrier.

Furthermore, the present invention provide an anti-trypanosoma preventing agent and treating agent comprising at least one of a compound represented by the above described formula (I), an optical isomer thereof and a pharmaceutically acceptable salt thereof as an active ingredient.

In addition, the present invention provides use of at least one of a compound represented by the above described formula (I), an optical isomer thereof and a pharmaceutically acceptable salt thereof in producing an antitrypanosoma preventing agent and treating agent.

Moreover, the present invention provides a method of preventing or treating the disease caused by Trypanosoma comprising administering an effective amount of at least one of a compound represented by the above described formula (I), an optical isomer thereof and a pharmaceutically acceptable salt thereof to a patient requiring treatment.

As the compound of the present invention, for example, the following compounds can be enumerated.

Compounds A of claim 1 represented by the above described formula (I), wherein X is a hydrogen atom;

$R^1$ is a hydrogen atom;

$R^2$ is a $C_{1-4}$ alkyl group;

$R^3$ is —CHO; and $R^4$ is —CH(OH)—$(CH_2)_q$—$CH_3$ (wherein q is an integer of 1 to 12), optical isomers thereof and pharmaceutically acceptable salts thereof.

Compounds B of claim 1 represented by the above described formula (I), wherein X is a halogen atom;

$R^1$ is a hydrogen atom;

$R^2$ is a $C_{1-4}$ alkyl group;

$R^3$ is —CHO; and $R^4$ is —CH(OH)—$(CH_2)_q$—$CH_3$ (wherein q is an integer of 1 to 12), optical isomers thereof and pharmaceutically acceptable salts thereof.

Compounds C of claim 1 represented by the above described formula (I), wherein X is a hydrogen atom or a halogen atom;

$R^1$ is a hydrogen atom;

$R^2$ is a hydrogen atom or a $C_{1-4}$ alkyl group;

$R^3$ is —CHO; and $R^4$ is —CH=CH—$(CH_2)_p$—$CH_3$ (wherein p is an integer of 1 to 12), optical isomers thereof and pharmaceutically acceptable salts thereof.

In addition to the above described compounds, the following compounds can be enumerated.

[Formula 3-1]

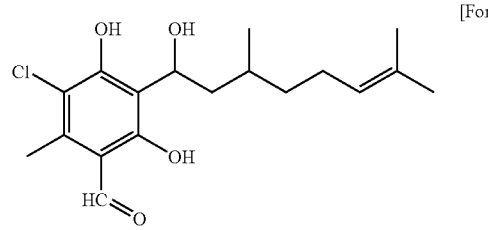

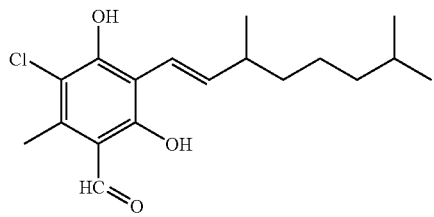

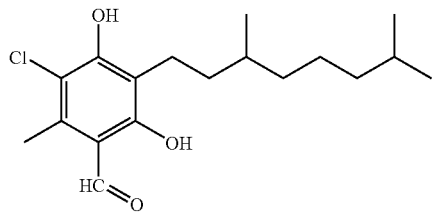

[Formula 3-2]

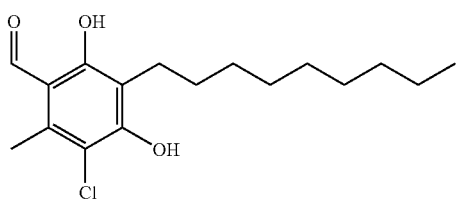

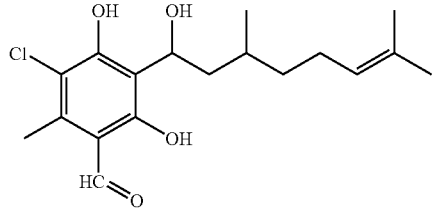

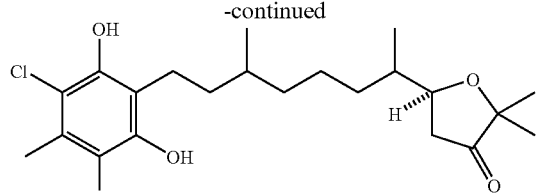

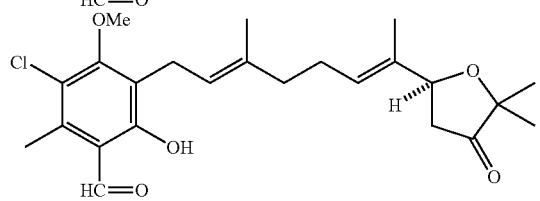

[Formula 3-3]

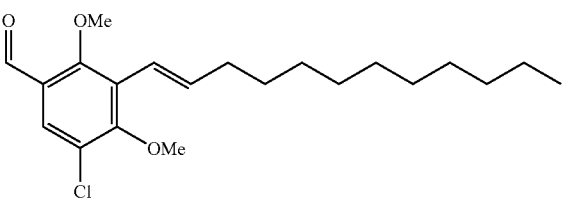

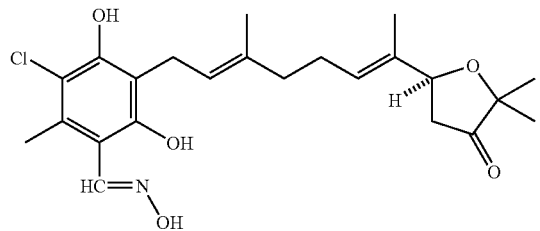

The foregoing compounds are examples of the compounds of claim 1.

The inhibition effect of the novel halogen-containing phenol derivatives having an alkyl side chain on the glycerol-3-phosphate-dependent respiration in the mitochondrial specimen prepared by mechanically crushing the bodies of Trypanosoma brucei brucei multiplied in the rat bloodstream with glass beads and subjecting the crushed bodies to centrifugal fractionation was examined. While the absolute amounts of 50% inhibition of antimycin A3, myxothiazol and stigmatellin which are known as Q cycle inhibitors are 48,600, 21,500 and 18,600 pmol/mg protein, respectively, the novel halogen-containing phenol compounds having an alkyl side chain singly exhibits the inhibition effect at a lower concentration than ascofuranone. Further, it has been found that the addition of glycerin exhibits at least the same degree of effect as ascofuranone.

EFFECT OF THE INVENTION

The compounds of the present inventions have such an advantage that they exhibit the same degree of the above described inhibition effect as ascofuranone at a lower concentration than ascofuranone and the addition of glycerin exhibits at least the same degree of effect as ascofuranone at a lower concentration than ascofuranone.

BEST MODE FOR CARRYING OUT THE INVENTION

In the present invention, $C_{1-7}$ alkyl group means a straight chain or branched chain alkyl group having 1 to 3 carbon atoms and includes, for example, a methyl group, an ethyl group, an n-propyl group, an i-propyl group, an n-butyl group, an i-butyl group, an s-butyl group, a t-butyl group, an n-pentyl group, an n-hexyl. group and an n-heptyl group.

In the present invention, $C_{1-4}$ alkyl group means a straight chain or branched chain alkyl group having 1 to 4 carbon atoms and includes, for example, a methyl group, an ethyl group, an n-propyl group, an i-propyl group, an n-butyl group, an i-butyl group, an s-butyl group and a t-butyl group.

In the present invention, $C_{1-4}$ alkoxy group means a group represented by "$C_{1-4}$ alkyl group-O—" and the $C_{1-4}$ alkyl group means the same as defined above. The $C_{1-4}$ alkoxy group includes, for example, a methoxy group, an ethoxy group, an n-propoxy group, an i-propoxy group, an n-butoxy group, an i-butoxy group, an s-butoxy group and a t-butoxy group.

In the present invention, $C_{1-3}$ alkoxycarbonyl group means a group represented by "$C_{1-4}$ alkoxy group-CO—" and the $C_{1-4}$ alkyl group means the same as defined above. The $C_{1-4}$ alkoxycarbonyl group includes, for example, a methoxycarbonyl group, an ethoxycarbonyl group, an n-propoxycarbonyl group, an i-propoxycarbonyl group, an n-butoxycarbonyl group, an i-butoxycarbonyl group, an s-butoxycarbonyl group and a t-butoxycarbonyl group.

In the present invention, a phenoxyalkyl group means a group represented by "phenyl group-O—$C_{1-4}$ alkyl group" and includes, for example, a phenoxymethyl group and a phenoxyethyl group.

The compounds of the present invention can be produced, for example, by the following method.

[Formula 4]

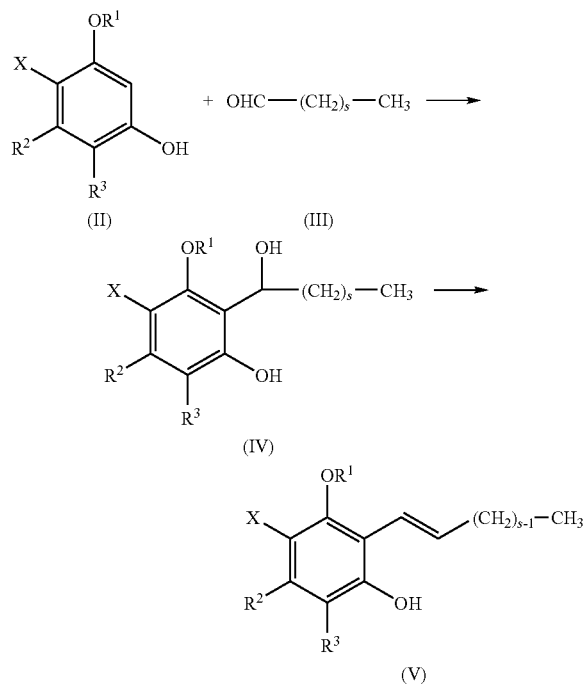

The compound of formula (II) (wherein X, $R^1$, $R^2$ and $R^3$ are the same as defined above) is reacted with an aldehyde of formula (III) (wherein s is an integer of 1 to 13) to obtain a compound for formula (IV). Furthermore, the compound of formula (IV) is subjected to dehydration reaction to obtain a compound of formula (V). In addition, by hydrogenating the double bond in the side chain in the compound of formula (V), —$CH_2$—$CH_2$—$(CH_2)_{s-1}$—$CH_3$, that is, —$(CH_2)_{s+1}$—$CH_3$ can be formed. This side chain [—$(CH_2)_{s+1}$—$CH_3$], —CH(OH)—$(CH_2)_s$—$CH_3$ in the compound of formula (IV) and —$CH_2$—$CH_2$—$(CH_2)_{s-1}$—$CH_3$ in the compound of formula (V) correspond to $R^4$ in the above described formula (I).

In the following, the general methods for preparing compounds A to D will be described.

(1) Compounds A and Compounds B

A compound represented by formula (II) and an aldehyde represented by formula (III): OHC—$(CH_2)_s$—$CH_3$ are stirred in the presence of a Lewis acid (a catalytic amount to 1 equivalent amount) such as magnesium chloride, calcium chloride, barium chloride and samarium chloride and 0.1 to 1 M of a base using water, an organic solvent or a water-organic solvent mixed system as a solvent at a temperature ranging from 0° C. to room temperature for 5 to 24 hours. Here, as the base, a hydroxide such as lithium hydroxide, sodium hydroxide, potassium hydroxide, calcium hydroxide and barium hydroxide and, in addition, an organic base such as triethylamine, pyridine, 4-dimethylaminopyridine and diazabicyclo [5.4.0]undeca-7-ene can be suitably selected. As the organic solvent, an alcohol such as ethylene glycol, methanol, ethanol and propanol and an ether such as dioxane and tetrahydrofuran can be suitably selected. The reaction mixture is made acidic with hydrochloric acid and extracted with an organic solvent such as ether, ethyl acetate and chloroform, and the extract is dried, concentrated, and thereafter purified by silica gel,thin-layer chromatography to produce a compound of formula (I), wherein $R^4$ is —CH(OH)—$(CH_2)_q$—$CH_3$ (wherein q is an integer of 1 to 13) according to this application.

(2) Compounds C

The compound of formula (I) wherein $R^4$ is —CH(OH)—$(CH_2)_q$—$CH_3$ (wherein q is an integer of 1 to 13) according to this application obtained in the above (1) is stirred in the presence of an acid (a catalytic amount to 10 equivalent amount) such as hydrochloric acid, nitric acid, sulfuric acid and phosphoric acid in acetic acid at a temperature ranging from room temperature to a reflux temperature for one to five hours. The reaction mixture is extracted with an organic solvent such as ether, ethyl acetate, chloroform at room temperature, and the extract is dried, concentrated, and thereafter purified by silica gel thin-layer chromatography to produce a compound of formula (I), wherein $R^4$ is —CH=CH—$(CH_2)_p$—$CH_3$ (wherein p is an integer of 1 to 12) according to this application.

(3) Compounds D

The compound of formula (I), wherein $R^4$ is —CH=CH—$(CH_2)_p$—$CH_3$ (wherein p is an integer of 1 to 12) obtained in the above described (2) according to this application is stirred in the presence of a catalyst such as platinum and palladium/carbon with the use of a solvent including an alcohol such as ethylene glycol, methanol, ethanol and propanol, an ether such as dioxane and tetrahydrofuran, an ester such as ethyl acetate and butyl acetate and an acid such as acetic acid and propionic acid at a temperature ranging from 0C to a reflux temperature in a hydrogen atmosphere for one to ten hours. The reaction mixture is concentrated, and then purified by silica gel thin-layer chromatography to produce a compound of formula (I), wherein $R^4$ is —$(CH_2)_r$—$CH_3$ (wherein r is an integer of 1 to 14, and when r is 8, the compound comes to a compound of this application).

Among the compounds of the present invention, there exist optical isomers, and the present invention comprises all respective optical isomers and mixtures thereof. The pharmaceutical composition of the present invention may use any of them. Further, the optical isomers can be obtained by resolution of the racemate by well-known methods including, for example, a preferential crystallization method, a column chromatography using an optically active stationary phase and a method of obtaining diastereomers.

The pharmaceutically acceptable salts of the compounds of the present invention or their optical isomers include, for example, the following salts.

In the case of the salt of the phenolic OH, the sodium salt, potassium salt, lithium salt, ammonium salt and the like are enumerated.

When $R^3$ is COOH, the sodium salt, potassium salt, lithium salt, ammonium salt and the like are enumerated.

As the carrier which is used in the pharmaceutical composition of the present invention, any additive that is well-known in the technical field of drug production can be used. Such a carrier includes, for example, a filler, a diluent, a moistening agent, a suspension, an emulsifying agent, a dispersing agent, an auxiliary, a sweetener, a coloring agent, a flavor, a buffer agent, an antiseptic, a preservative, a buffer agent, a binder and a stabilizer, and in accordance with the target dosage form, a necessary carrier can be selected from the well-known, customarily used carriers. For example, a salt of an alkaloid having an indole skeleton with an acid and a salt of ascofuranone with a base are dissolved in water or mixed with a suspension, a filler and/or other carriers and made into a preparation in the form of a dosage form suitable for oral administration. Further, the filler or the auxiliary includes, for example, lactose, various types of starch (for example, corn starch), chitin, chitosan, glucose, sucrose, cellulose, methyl cellulose, carboxymethyl cellulose, magnesium stearate, a lauryl sulfate salt, talc, a vegetable oil (for example, soybean oil, peanut oil. and olive oil) and lecithin.

Further, the pharmaceutical composition of the present invention may contain glycerin. The amount of glycerin added can be suitably adjusted depending on the situation.

The dose of each compound relating to the present invention varies depending on the morbid state and symptom, and since Trypanosoma parasitically lives on the intestinal tract, oral administration is preferred, and the object can be obtained in an amount of 10 to 1,000 mg/kg body weight. When the compounds of the present invention are used as drugs, they are preferably made into preparations suitable for oral administration such as tablets, capsules and dosage forms obtained by neutralizing the compounds with an alkali to solubilize them in water or by mixing them with a suspension, a filler or its auxiliary. Further, enteric coated tablets which prevent the decomposition of the compounds in the stomach to allow them to reach the intestine tract without their decomposition. The enteric coated tablets can be produced by using lactose, various types of starch, glucose, fructosecellulose, methyl cellulose, carboxymethyl cellulose, magnesium stearate, a lauryl sulfate salt, talc, a vegetable oil, lecithin or the like as a filler or its auxiliary.

EXAMPLES

The present invention will now be explained in detail based on examples but these examples do not in any way limit the present invention.

Example 1

2,4-Dihydroxy-3-(1-hydroxydodecyl)-6-methylbenzaldehyde (Compound No.: 195-12)

2,4-Dihydroxy-6-methylbenzaldehyde (91 mg, 0.60 mmol) described in M. M. Joullie et al., J. Org. Chem., 50, 3997 (1985), dodecanal (133 mg, 0.72 mmol) and calcium chloride dihydrate (59 mg, 0.40 mmol) were stirred in a 0.4 M potassium hydroxide methanol solution (2 ml) at 0° C. for 24 hours. The reaction mixture was made acidic with 1 M hydrochloric acid. After extractive workup with ethyl acetate, the crude product was purified by silica gel thin-layer chromatography (hexane:ethyl acetate=3:1) to obtain 2,4-dihydroxy-3-(1-hydroxydodecyl)-6-methylbenzaldehyde (58 mg, yield 28%).

[Formula 5]

2,4-Dihydroxy-3-(1-hydroxydodecy)-6-methylbenzaldehyde (195-12)

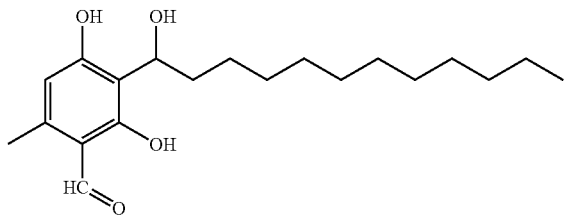

$^1$H NMR (CDCl$_3$) δ 0.88 (t, J=6.9 Hz, 3H, —(CH$_2$)$_{10}$CH$_3$), 1.2-1.6 (m, 18H, —CH$_2$—(CH$_2$)$_9$CH$_3$), 1.72-1.88 (m, 2H, C(3)-CH(OH)—CH$_2$—), 2.49 (s, 3H, C(6)-CH$_3$), 2.55 d, J=3.5 Hz, 1H, C(3)—CHOH—), 5.36-5.41 (m, 1H, C(3)—CH(OH)—), 6.24 (s, 1H, C(5)-H), 9.53. (s, 1H, C(4)-OH), 10.04 (s, 1H, CHO), 12.76 (s, 1H, C(2)-OH); IR (neat) 3300-3500, 2950, 2850, 1636, 1278, 1234, 1192, 591 cm$^{-1}$.

In addition to this compound, 2,4-dihydroxy-3-(1-hydroxypropyl)-6-methylbenzaldehyde (195-3), 2,4-dihydroxy-3-(1-hydroxypentyl)-6-methylbenzaldehyde (195-5), 2,4-dihydroxy-3-(1-hydroxyheptyl)-6-methylbenzaldehyde (195-7), 2,4-dihydroxy-3-(1-hydroxynonyl)-6-methylbenzaldehyde (195-9) and 2,4-dihydroxy-3-(1-hydroxydecyl)-6-methylbenzaldehyde (195-10) were synthesized by the same reaction with the use of respective corresponding starting raw materials.

Example 2

2,4-Dihydroxy-3-(1-hydroxypropyl)-6-methylbenzaldehyde (Compound No.: 195-3)

[Formula 6]

2,4-Dihydroxy-3-(1-hydroxypropyl)-6-methylbenzaldehyde (195-3)

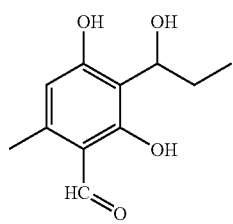

195-3

$^1$H NMR (CDCl$_3$) δ 1.01 (t, J=7.2 Hz, 3H, —CH$_2$CH$_3$), 1.77-1.91 (m, 2H, —CH$_2$CH$_3$), 2.48 (s, 3H, C(6)-CH$_3$), 2.69 (d, J=3.5 Hz, 1H, C(3)-CHOH—), 5.28 (ddd, J=3.5, 5.2, 8.0 Hz, 1H, C(3)-CHOH—), 6.23 (s, 1H, C(5)-H), 9.57 (s, 1H, C(4)-OH), 10.02 (s, 1H, CHO), 12.75 (s, 1H, C(2)-OH)); IR (KBr): 3200-3500, 2934, 1630, 1580, 1285, 1232, 1185, 1169 cm$^{-1}$.

Example 3

2,4-Dihydroxy-3-(1-hydroxypentyl)-6-methylbenzaldehyde (Compound No.: 195-5)

[Formula 7]

2,4-Dihydroxy-3-(1-hydroxypentyl)-6-methylbenzaldehyde (195-5)

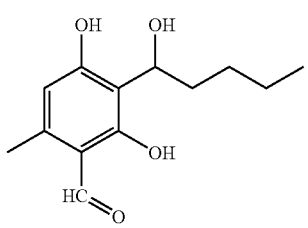

195-5

$^1$H NMR (CDCl$_3$) δ 0.91 (t, J=7.2 Hz, 3H, —(CH$_2$)$_2$CH$_3$), 1.3-1.5 (m, 4H, —(CH$_2$)$_2$CH$_3$), 1.72-1.90 (m, 2H, C(3)-CH(OH)—CH$_2$—), 2.48 (s, 3H, C(6)-CH$_3$), 2.73 (d, J=3.4 Hz, 1H, C(3)-CHOH—), 5.38 (ddd, J=3.4, 4.6, 8.1 Hz, 1H, C(3)-CHOH—), 6.23 (s, 1H, C(5)-H), 9.57 (s, 1H, C(4)-OH), 10.03 (s, 1H, CHO), 12.75 (s, 1H, C(2)-OH)); IR (neat): 3100-3500, 2950, 2932, 2872, 1715, 1630, 1370, 1286, 1232, 1192 cm$^{-1}$.

Example 4

2,4-Dihydroxy-3-(1-hydroxyheptyl)-6-methylbenzaldehyde (Compound No.: 195-7)

[Formula 8]

2,4-Dihydroxy-3-(1-hydroxyheptyl)-6-methylbenzaldehyde (195-7)

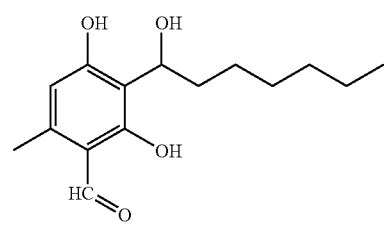

195-7

$^1$H NMR (CDCl$_3$) δ 0.89 (t, J=6.9 Hz, 3H, —(CH$_2$)$_4$CH$_3$), 1.23-1.50 (m, 8H, —(CH$_2$)$_4$CH$_3$), 1.72-1.88 (m, 2H, C(3)-CH(OH)—CH$_2$—), 2.49 (s, 3H, C(6)-CH$_3$), 2.54 (d, J=3.3 Hz, 1H, C(3)-CHOH—), 5.39 (ddd, J=3.3, 4.8, 8.1 Hz, 1H, C(3)-CHOH—), 6.24 (s, 1H, C(5)-H), 9.51 (s, 1H, C(4)-OH), 10.04 (s, 1H, CHO), 12.76 (s, 1H, C(2)-OH)); IR (neat): 3100-3500, 2935, 2862, 1707, 1630, 1369, 1281, 1236, 1192 cm$^{-1}$.

Example 5

2,4-Dihydroxy-3-(1-hydroxynonyl)-6-methylbenzaldehyde (Compound No.: 195-9)

(Formula 9)

2,4-Dihydroxy-3-(1-hydroxynonyl)-6-methylbenzaldehyde (195-9)

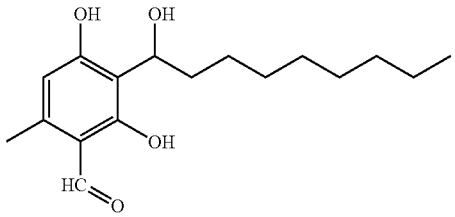

195-9

$^1$H NMR (CDCl$_3$) δ 0.85 (t, J=6.2 Hz, 3H, —(CH$_2$)$_7$CH$_3$), 1.1-1.6 (m, 12H, —CH$_2$—(CH$_2$)$_6$CH$_3$), 1.72-1.88 (m, 2H, C(3)-CH(OH)—CH$_2$—), 2.49 (s, 3H, C(6)-CH$_3$), 2.54 (br s, 1H, C(3)-CHOH—), 5.36 (dd, J=5.1, 7.8 Hz, 1H, C(3)-CHOH—), 6.22 (s, 1H, C(5)-H), 9.56 (br s, 1H, C(4)-OH), 10.01 (s, 1H, CHO), 12.72 (s, 1H, C(2)-OH)); IR (KBr): 3200-3600, 2925, 2855, 1632, 1288, 1234, 1192 cm$^{-1}$.

Example 6

2,4-Dihydroxy-3-(1-hydroxydecyl)-6-methylbenzaldehyde (Compound No.: 195-10)

[Formula 10]

2,4-Dihydroxy-3-(1-hydroxydecyl)-6-methylbenzaldehyde (195-10)

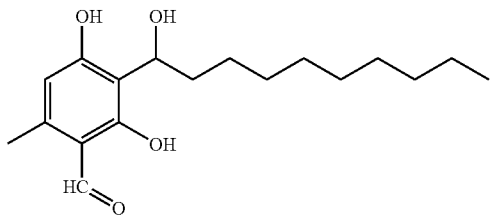

$^1$H NMR (CDCl$_3$) δ 0.86 (t, J=6.5 Hz, 3H, —(CH$_2$)$_8$CH$_3$), 1.2-1.6 (m, 14H, —CH$_2$—(CH$_2$)$_7$CH$_3$), 1.6-1.9 (m, 2H, C(3)-CH(OH)—CH$_2$—), 2.48 (s, 3H, C(6)-CH$_3$), 2.73 (br s, 1H, C(3)-CHOH—), 5.36 (dd, J=5.3, 7.7 Hz, 1H, C(3)-CHOH—), 6.22 (s, 1H, C(5)-H), 9.56 (s, 1H, C(4)-OH), 10.01 (s, 1H, CHO), 12.72 (s, 1H, C(2)-OH); IR (neat) 3200-3500, 2928, 2858, 1624, 1468, 1360, 1285, 1232, 1196, 781 cm$^{-1}$.

Example 7

5-Chloro-2,4-dihydroxy-3-(1-hydroxydodecyl)-6-methyl-benzaldehyde (Compound No.: 196-12)

5-Chloro-2,4-dihydroxy-6-methylbenzaldehyde (112 mg, 0.60 mmol) described in M. M. Joullie et al., J. Org. Chem., 50, 3997 (1985), dodecanal (133 mg, 0.72 mmol) and calcium chloride dihydrate (58 mg, 0.40 mmol) were stirred in a 0.4 M potassium hydroxide methanol solution (2 ml) at 0° C. for 24 hours. The reaction mixture was made acidic with 1 M hydrochloric acid, extracted with ethyl acetate, and after post-treatment, the crude product was purified by silica gel thin-layer chromatography (chloroform:ethyl acetate=15:1) to obtain 5-chloro-2,4-dihydroxy-6-methylbenzaldehyde (68 mg, recovery 61%) and 5-chloro-2,4-dihydroxy-3-(1-hydroxydodecyl)-6-methylbenzaldehyde (45 mg, yield 20%).

[Formula 11]

5-Chloro-2,4-dihydroxy-3-(1-hydroxydodecyl)-6-methylbenzaldehyde (196-12)

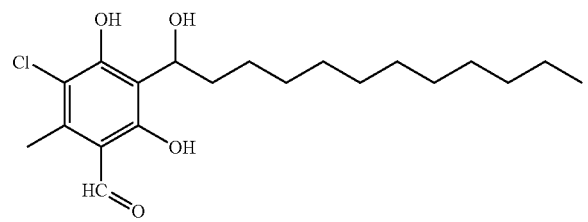

$^1$H NMR (CDCl$_3$) δ 0.88 (t, J=6.6 Hz, 3H, —(CH$_2$)$_{10}$CH$_3$), 1.15-1.55 (m, 18H, —CH$_2$—(CH$_2$)$_9$CH$_3$), 1.65-1.91 (m, 2H, C(3)-CH(OH)—CH$_2$—), 2.59 (s, 3H, C(6)-CH$_3$), 3.09 (br s, 1H, C(3)-CH(OH)—), 5.34 (dd, J=5.0, 7.7 Hz, 1H, C(3)-CH(OH)CH$_2$), 9.90 (br s, 1H, C(4)-OH), 10.08 (s, 1H, CHO), 12.79 (s, 1H, C(2)-OH); IR (KBr): 3000-3600, 2928, 2860, 1624, 1460, 1373, 1285, 1225 cm$^{-1}$.

In addition to this compound, 5-chloro-2,4-dihydroxy-3-(1-hydroxypropyl)-6-methylbenzaldehyde (196-3), 5-chloro-2,4-dihydroxy-3-(1-hydroxypentyl)-6-methylbenzaldehyde (196-5), 5-chloro-2,4-dihydroxy-3-(1-hydroxyheptyl)-6-methylbenzaldehyde (196-7), 5-chloro-2,4-dihydroxy-3-(1-hydroxynonyl)-6-methylbenzaldehyde (196-9) and 5-chloro-2,4-dihydroxy-3-(1-hydroxydecyl)-6-methylbenzaldehyde (196-10) were synthesized by the same reaction with the use of respective corresponding starting raw materials.

Example 8

5-Chloro-2,4-dihydroxy-3-(1-hydroxypropyl)-6-methylbenzaldehyde (Compound No.: 196-3)

[Formula 12]

5-Chloro-2,4-dihydroxy 3-(1-hydroxypropyl)-6-methylbenzaldehyde (196-3)

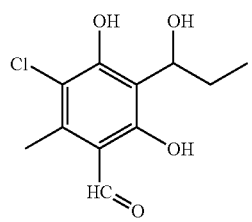

$^1$H NMR (CDCl$_3$) δ 1.00 (t, J=7.5 Hz, 3H, —CH$_2$CH$_3$), 1.75-1.91 (m, 2H, —CH$_2$CH$_3$), 2.59 (s, 3H, C(6)-CH$_3$), 3.31 (br s, 1H, C(3)-CHOH—), 5.28 (dd, J=5.4, 7.4 Hz, 1H, C(3)-CHOH—), 10.00 (br s, 1H, C(4)-OH), 10.08 (s, 1H, CHO), 12.79 (s, 1H, C(2)-OH)); IR (KBr): 3100-3600, 2980, 2935, 1620, 1373, 1286, 1225, 1138 cm$^{-1}$.

Example 9

5-Chloro-2,4-dihydroxy-3-(1-hydroxypentyl)-6-methylbenzaldehyde (Compound No.: 196-5)

[Formula 13]

2,4-Dihydroxy-3-(1-hydroxypentyl)-6-methylbenzaldehyde (196-5)

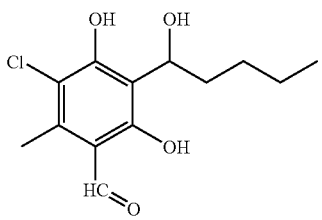

$^1$H NMR (CDCl$_3$) δ 0.91 (t, J=7.1 Hz, 3H, —(CH$_2$)$_2$CH$_3$), 1.3-1.5 (m, 4H, —(CH$_2$)$_2$CH$_3$), 1.72-1.90 (m, 2H, C(3)-CH(OH)—CH$_2$—), 2.61 (s, 3H, C(6)-CH$_3$), 2.96 (d, J=4.4 Hz, 1H, C(3)-CHOH—), 5.38 (dt, J=4.4, 8.0 Hz, 1H, C(3)-CHOH—), 9.90 (s, 1H, C(4)-OH), 10.02 (s, 1H, CHO), 12.82

(s, 1H, C(2)-OH)); IR (neat): 3100-3600, 2950, 2932, 2862, 1711, 1624, 1574, 1450, 1373, 1285, 1227, 1138, 758 cm$^{-1}$.

Example 10

5-Chloro-2,4-dihydroxy-3-(1-hydroxyheptyl)-6-methylbenz-aldehyde (Compound No.: 196-7)

[Formula 14]

2,4-Dihydroxy-3-(1-hydroxyheptyl)-6-methylbenzaldehyde (196-7)

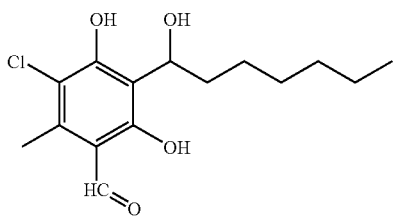

196-7

$^1$H NMR (CDCl$_3$) δ 0.87 (t, J=6.9 Hz, 3H, —(CH$_2$)$_4$CH$_3$), 1.23-1.53 (m, 8H, —(CH$_2$)$_4$CH$_3$), 1.69-1.88 (m, 2H, C(3)-CH(OH)—CH$_2$—), 2.58 (s, 3H, C(6)-CH$_3$), 3.69 (br s, 1H, C(3)-CHOH—), 5.32 (dd, J=4.8, 7.8 Hz, 1H, C(3)-CHOH—), 10.08 (s, 1H, CHO), 10.17 (br s, 1H, C(4)-OH), 12.78 (s, 1H, C(2)-OH)); IR (neat): 3100-3500, 2935, 2862, 1715, 1626, 1450, 1369, 1288, 1225, 1136 cm$^{-1}$.

Example 11

5-Chloro-2,4-dihydroxy-3-(1-hydroxynonyl)-6-methylbenzaldehyde (Compound No.: 196-9)

[Formula 15]

5-Chloro-2,4-dihydroxy-3-(1-hydroxynonyl)-6-methylbenzaldehyde (196-9)

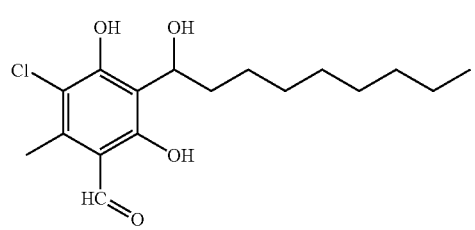

196-9

$^1$H NMR (CDCl$_3$) δ 0.87(t, J=6.8 Hz, 3H, —(CH$_2$)$_7$CH$_3$), 1.2-1.6 (m, 12H, —CH$_2$—(CH$_2$)$_6$CH$_3$), 1.69-1.94 (m, 2H, C(3)-CH(OH)—CH$_2$—), 2.61 (s, 3H, C(6)-CH$_3$), 2.80 (d, J=3.5 Hz, 1H, C(3)-CH(OH)CH$_2$), 5.33-5.41 (m, 1H, C(3)-CH(OH)CH$_2$), 9.82 (s, 1H, C(4)-OH), 10.11 (s, 1H, CHO), 12.81 (s, 1H, C(2)-OH); IR (KBr): 3000-3600, 2928, 2858, 1624, 1454, 1373, 1285, 1231 cm$^{-1}$.

Example 12

5-Chloro-2,4-dihydroxy-3-(1-hydroxydecyl)-6-methylbenzaldehyde (Compound No.: 196-10)

[Formula 16]

5-Chloro-2,4-dihydroxy-3-(1-hydroxydecyl)-6-methylbenzaldehyde (196-10)

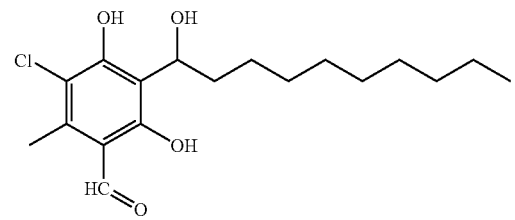

196-10

$^1$H NMR (CDCl$_3$) δ 0.87 (t, J=6.6 Hz, 3H, —(CH$_2$)$_8$CH$_3$), 1.15-1.55 (m, 14H, —CH$_2$—(CH$_2$)$_7$CH$_3$), 1.65-1.90 (m, 2H, C(3)-CH(OH)—CH$_2$—), 2.58 (s, 3H, C(6)-CH$_3$), 3.15 (br s, 1H, C(3)-CH(OH)CH$_2$), 5.33 (dd, J=5.1, 8.1 Hz, 1H, C(3)-CH(OH)CH$_2$), 9.92 (br s, 1H, C(4)-OH), 10.08 (s, 1H, CHO), 12.78 (s, 1H, C(2)-OH); IR(KBr): 3000-3600, 2922, 2858, 1618, 1450, 1371, 1285, 1231 cm$^{-1}$.

Example 13

5-Chloro-3-(1-dodecenyl)-2,4-dihydroxy-6-methylbenzaldehyde (Compound No.: 200-12)

5-Chloro-2,4-dihydroxy-3-(1-hydroxydodecyl)-6-methylbenzaldehyde (33 mg, 0.089 mmol) was stirred in acetic acid (2 ml) in the presence of 85% phosphoric acid (0.024 mmol) at a reflux temperature for 1.5 hours. The reaction mixture was cooled to room temperature. After extractive workup with ethyl acetate, the crude product was purified by silica gel thin-layer chromatography (chloroform) to obtain 5-chloro-3-(1-dodecenyl)-2,4-dihydroxy-6-methylbenzaldehyde (24 mg, yield 76%).

[Formula 17]

5-Chloro-3-(1-dodecenyl)-2,4-dihydroxy-6-methylbenzaldeyde (200-12)

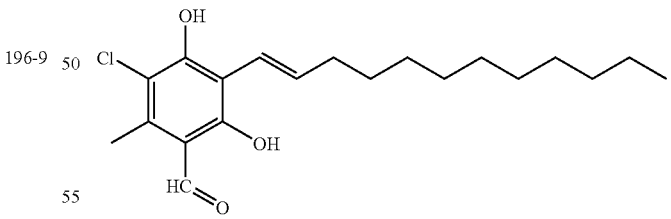

200-12

$^1$H NMR (CDCl$_3$) δ 0.88 (t, J=6.6 Hz, 3H, —(CH$_2$)$_7$CH$_3$), 1.22-1.40 (m, 14H, —(CH$_2$)$_7$CH$_3$), 1.43-1.55 (m, 2H, C(3)-CH=CH—CH$_2$—CH$_2$—), 2.22-2.30 (m, 2H, C(3)-CH=CH—CH$_2$—), 2.62 (s, 3H, C(6)-CH$_3$), 6.52 (d, J=16.2 Hz, 1H, C(3)-CH=CH—CH$_2$—), 6.57 (s, 1H, C(4)-OH), 6.65 (dt, J=6.5, 16.2 Hz, C(3)-CH=CH—CH$_2$—), 10.15 (s, 1H, CHO), 13.04 (s, 1H, C(2)-OH); IR(KBr) 3200-3600, 2915, 2849, 1617, 1419, 1283, 1228, 1141, 975 cm$^{-1}$.

In addition to this compound, 3-(1-decenyl)-2,4-dihydroxybenzaldehyde (197-10), 3-(1-dodecenyl)-2,4-dihydroxy-6-methylbenzaldehyde (198-12), 5-chloro-2,4-dihydroxy-6-methyl-3-(1-propenyl)benzaldehyde (200-3), 5-chloro-2,4-dihydroxy-6-methyl-3-(1-pentenyl)benzaldehyde (200-5), 5-chloro-3-(1-heptenyl)-2,4-dihydroxy-6-methylbenzaldehyde (200-7), 5-chloro-2,4-dihydroxy-6-methyl-3-(1-nonenyl)benzaldehyde (200-9) and 5-chloro-3-(1-decenyl)-2,4-dihydroxy-6-methylbenzaldehyde (200-10) could be obtained from respective corresponding alcohols by the same reaction.

Example 14

3-(1-Decenyl)-2,4-dihydroxybenzaldehyde (Compound No.: 197-10)

[Formula 18]

3-(1-Decenyl)-2,4-dihydroxybenzalehyde (197-10)

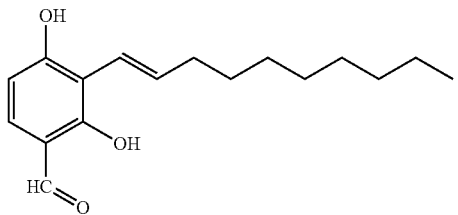

Mp 60-62° C.
$^1$H NMR (CDCl$_3$) δ 0.88 (t, J=6.9 Hz, 3H, —(CH$_2$)$_5$CH$_3$), 1.15-1.44 (m, 10H, —(CH$_2$)$_5$CH$_3$), 1.44-1.56 (m, 2H, C(3)-CH=CH—CH$_2$—CH$_2$—), 2.24-2.35 (m, 2H, C(3)-CH=CH—CH$_2$—), 6.24 (dt, J=6.6, 16.5 Hz, 1H, C(3)-CH=CH—CH$_2$—), 6.35 (br s, 1H, C(4)-OH), 6.41 (d, J=16.5 Hz, 1H, C(3)-CH=CH—CH$_2$), 6.56 (d, J=8.6 Hz, 1H, C(5)-H), 7.31 (d, J=8.6 Hz, 1H, C(6)-H), 9.70 (s, 1H, CHO), 11.83 (s, 1H, C(2)-OH); IR(KBr) 3100-3600, 2926, 2852, 1611, 1490, 1317, 1255, 975 cm$^{-1}$.

Example 15

3-(1-Dodecenyl)-2,4-dihydroxy-6-methylbenzaldehyde (Compound No.: 198-12)

[Formula 19]

3-(1-Dodecenyl)-2,4-dihydroxy-6-methylbenzaldehyde (198-12)

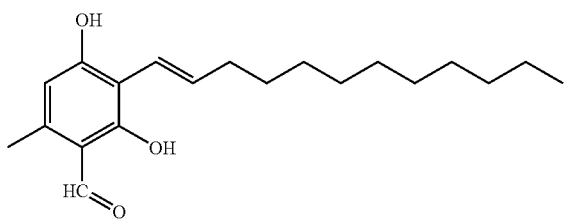

Mp 103-105° C.
$^1$H NMR (CDCl$_3$) δ 0.88 (t, J=6.6 Hz, 3H, —(CH$_2$)$_7$CH$_3$), 1.18-1.40 (m, 14H, —(CH$_2$)$_7$CH$_3$), 1.44-1.54 (m, 2H, C(3)-CH=CH—CH$_2$—CH$_2$—), 2.23-2.32 (m, 2H, C(3)-CH=CH—CH$_2$—), 2.51 (s, 3H, C(6)-CH$_3$), 6.15 (dt, J=6.6, 16.5 Hz, 1H, C(3)-CH=CH—CH$_2$—), 6.26 (br s, 1H, C(4)-OH), 6.30 (s, 1H, C(5)-H), 6.38 (d, J=16.5 Hz, 1H, C(3)-CH=CH—CH$_2$—), 10.09 (s, 1H, C(1)-CHO), 12.81 (s, 1H, C(2)-OH); IR(KBr) 3100-3500, 2920, 2851, 1602, 1257, 975 cm$^{-1}$.

Example 16

5-Chloro-2,4-dihydroxy-6-methyl-3-(1-propenyl)benzaldehyde (Compound No.: 200-3)

[Formula 20]

5-Chloro-2,4-dihydroxy-6-methyl-3-(1-propenyl)benzaldeyde (200-3)

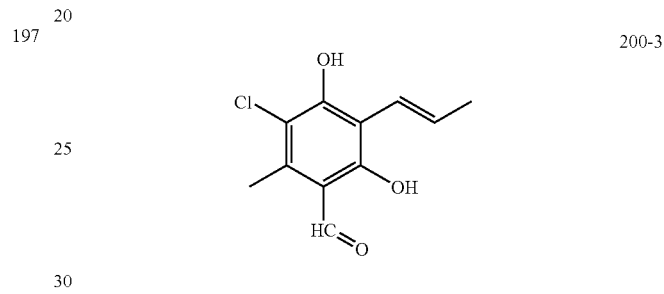

Mp 119-121° C.
$^1$H NMR (CDCl$_3$) δ 1.96 (d, J=6.4 Hz, 3H, —CH=CH—CH$_3$), 2.62 (s, 3H, C(6)-CH$_3$), 6.55 (d, J=16.1 Hz, 1H, C(3)-CH=CH—CH$_3$), 6.58 (s, 1H, C(4)-OH), 6.67 (dq, J=6.4, 16.1 Hz, 1H, C(3)-CH=CH—CH$_3$), 10.15 (s, 1H, CHO), 13.05 (s, 1H, C(2)-OH); IR(KBr): 3200-3600, 2926, 1620, 1415, 1286, 1258, 1130, 978, 793 cm$^{-1}$.

Example 17

5-Chloro-2,4-dihydroxy-6-methyl-3-(1-pentenyl)benzaldehyde (Compound No.: 200-5)

[Formula 21]

5-Chloro-2,4-dihydroxy-6-methyl-3-(1-pentenyl)benzaldeyde (200-5)

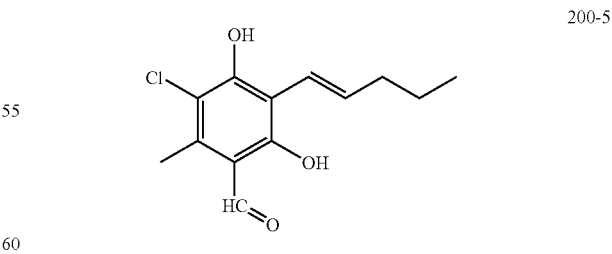

Mp 121-122° C.
$^1$H NMR (CDCl$_3$) δ 0.97 (t, J=7.3 Hz, 3H, —CH$_2$CH$_2$CH$_3$), 1.48-1.56 (m, 2H, —CH$_2$CH$_2$CH$_3$), 2.23-2.28 (m, 2H, C(3)-CH=CH—CH$_2$—), 2.62 (s, 3H, C(6)-CH$_3$), 6.53 (d, J=16.3 Hz, 1H, C(3)-CH=CH—CH$_2$—), 6.59 (s, 1H, C(4)-OH), 6.66 (dt, J=6.9, 16.3 Hz, C(3)-CH=CH—CH$_2$—), 10.15 (s, 1H, CHO), 13.06 (s, 1H, C(2)-OH); IR(KBr): 3100-3500, 2957, 2928, 1622, 1414, 1283, 1231, 1138, 1117, 984, 843, 791 cm$^{-1}$.

Example 18

5-Chloro-3-(1-heptenyl)-2,4-dihydroxy-6-methyl-benzaldehyde (Compound No.: 200-7)

[Formula 22]

5-Chloro-3-(1-heptenyl)-2,4-dihydroxy-6-methyl-benzaldeyde (200-7)

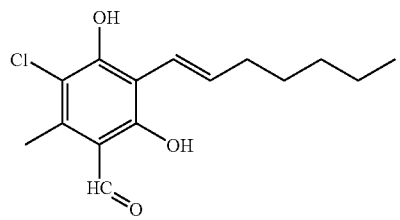

Mp 96-97° C.
$^1$H NMR (CDCl$_3$) δ 0.90 (t, J=7.1 Hz, 3H, —(CH$_2$)$_2$CH$_3$), 1.30-1.38 (m, 4H, —(CH$_2$)$_2$CH$_3$), 1.45-1.53 (m, 2H, C(3)-CH=CH—CH$_2$—CH$_2$—), 2.24-2.29 (m, 2H, C(3)-CH=CH—CH$_2$—), 2.62 (s, 3H, C(6)-CH$_3$), 6.53 (d, J=16.3 Hz, 1H, C(3)-CH=CH—CH$_2$—), 6.59 (s, 1H, C(4)-OH), 6.66 (dt, J=6.9, 16.3 Hz, C(3)-CH=CH—CH$_2$—), 10.15 (s, 1H, CHO), 13.06 (s, 1H, C(2)-OH); IR(KBr): 3100-3500, 2926, 2854, 1614, 1599, 1418, 1288, 1229, 1136, 980, 772 cm$^{-1}$.

Elemental Analysis (Found): C, 63.46; H, 6.66; Cl, 12.65%. (Calcd. for C$_{15}$H$_{19}$O$_3$Cl): C, 63.71; H, 6.77; Cl, 12.54%.

Example 19

5-Chloro-2,4-dihydroxy-6-methyl-3-(1-nonyl)ben-zaldehyde (Compound No.: 200-9)

[Formula 23]

5-Chloro-2,4-dihydroxy-6-methyl-3-(1-nonenyl)benzaldeyde (200-9)

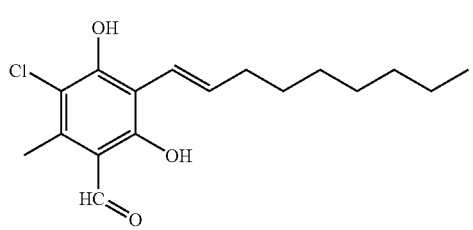

Mp 79.5-80.5° C.
$^1$H NMR (CDCl$_3$) δ 0.88 (t, J=6.5 Hz, 3H, —(CH$_2$)$_4$CH$_3$), 1.23-1.40 (m, 8H, —(CH$_2$)$_4$CH$_3$), 1.42-1.55 (m, 2H, C(3)-CH=CH—CH$_2$—CH$_2$—), 2.22-2.30 (m, 2H, C(3)-CH=CH—CH$_2$—), 2.62 (s, 3H, C(6)-CH$_3$), 6.52 (d, J=16.2 Hz, 1H, C(3)-CH=CH—CH$_2$—), 6.57 (s,. 1H, C(4)-OH), 6.65 (dt, J=6.5, 16.2 Hz, C(3)-CH=CH—CH$_2$—), 10.15 (s, 1H, CHO), 13.04 (s, 1H, C(2)-OH); IR(KBr): 3200-3600, 2922, 2850, 1614, 1416, 1232, 1134, 980, 793 cm$^{-1}$.

MS m/z 312 (M+2, 9), 310 (M$^+$, 25), 201 (35), 199 (100).

Example 20

5-Chloro-3-(1-decenyl)-2,4-dihydroxy-6-methylben-zaldehyde (Compound No.: 200-10)

[Formula 24]

5-Chloro-3-(1-decenyl)-2,4-dihydroxy-6-methylben-zaldeyde (200-10)

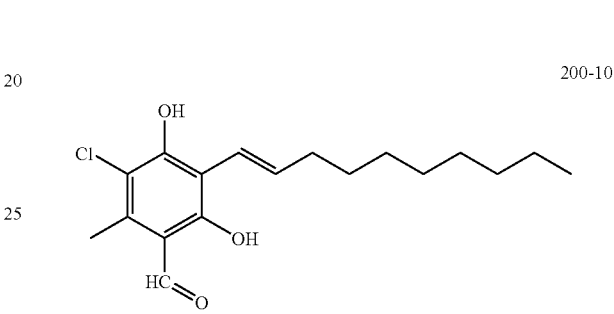

Mp 83-84° C.
$^1$H NMR (CDCl$_3$) δ 0.88 (t, J=6.8 Hz, 3H, —(CH$_2$)$_5$CH$_3$), 1.22-1.40 (m, 10H, —(CH$_2$)$_5$CH$_3$), 1.45-1.55 (m, 2H, C(3)-CH=CH—CH$_2$—CH$_2$—), 2.22-2.30 (m, 2H, C(3)-CH=CH—CH$_2$—), 2.62 (s, 3H, C(6)-CH$_3$), 6.52 (d, J=16.2 Hz, 1H, C(3)-CH=CH—CH$_2$—), 6.57 (s, 1H, C(4)-OH), 6.65 (dt, J=6.5, 16.2 Hz, C(3)-CH=CH—CH$_2$—), 10.15 (s, 1H, CHO), 13.04 (s, 1H, C(2)-OH); IR(KBr) 3200-3600, 2922, 2850, 1617, 1420, 1231, 1142, 975, 595 cm$^{-1}$.

Elemental Analysis (Found): C, 66.38; H, 7.60; Cl, 10.85%. (Calcd. for C$_{18}$H$_{25}$O$_3$Cl): C, 66.55; H, 7.76; Cl, 10.91%

Example 21

2,4-Dihydroxy-3-(1-hydroxydodecyl)benzaldehyde (Compound No.: 201-12)

[Formula 25]

2,4-Dihydroxy-3-(1-hydroxydodecyl)benzaldehyde (201-12)

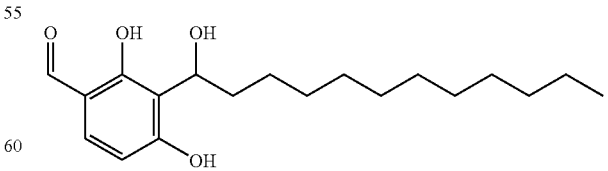

2,4-Dihydroxybenzaldehyde (1.39 g, 10.0 mmol), dodeca-nal (2.21 g, 12.0 mmol) and calcium chloride dehydrate (1.03 g, 7.0 mmol) were dissolved in methanol (21 ml), added with a potassium hydroxide methanol solution (1.0 M, 14 ml) at 0(C and stirred for 24 hours. The reaction mixture was made acidic with 1 M hydrochloric acid and extracted with ethyl acetate, and after post-treatment, the crude product (2.84 g) was purified by silica gel column chromatograophy (hexane: ethyl acetate=5:1) to obtain 2,4-dihydroxy-3-(1-hydroxydodecyl)benzaldehyde (colorless solid 1.65 g, yield 51%) and 2,4-dihydroxybenzaldehyde (552 mg, recovery 40%).

Mp 94-95° C.

$^1$H NMR (CDCl$_3$) 0.88 (t, J=6.8 Hz, 3H, —(CH$_2$)$_{10}$CH$_3$), 1.20-1.55 (m, 18H, —CH$_2$—(CH$_2$)$_9$CH$_3$), 1.73-1.91 (m, 2H, C(3)-CH(OH)—CH$_2$—), 2.59 (d, J=3.5 Hz, 1H, C(3)-CH(OH)—), 5.40-5.46 (m, 1H, C(3)-CH(OH)—), 6.50 (d, J=8.7 Hz, 1H, C(5)-H), 7.34 (d, J=8.7 Hz, 1H, C(6)-H), 9.59 (s, 1H), 9.66 (s, 1H), 11.78 (s, 1H, C(2)-OH); IR (KBr) 3200-3600, 2926, 2860, 1711, 1624, 1489, 1229 cm$^{-1}$.

Example 22

5-Chloro-2,4-dihydroxy-3-(1-hydroxydodecyl)benzaldehyde (Compound No.: 202-12)

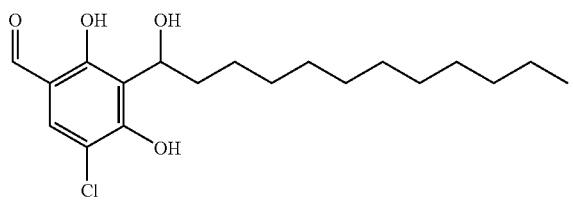

[Formula 26]

5-Chloro-2,4-dihydroxy-3-(1-hydroxydodecy)benzaldehyde (202-12)

5-Chloro-2,4-dihydroxybenzaldehyde (493 mg, 2.86 mmol), dodecanal (641 mg, 3.48 mmol) and calcium chloride dehydrate (3.02 mg, 2.03 mmol) were dissolved in methanol (6 ml), added with a potassium hydroxide methanol solution (1.0 M, 4.0 ml) at 0° C. and stirred for 24 hours. The reaction mixture was made acidic with 1 M hydrochloric acid and extracted with ethyl acetate, and after post-treatment, the crude product (1.18 g) was purified by silica gel column chromatography (hexane:ethyl acetate=7:1) to obtain 5-chloro-2,4-dihydroxy-3-(1-hydroxydodecyl)benzaldehyde (colorless solid 475 mg, yield 46%) and 5-chloro-2,4-dihydroxybenzaldehyde (209 mg, recovery 42%).

Mp 78-79° C.

$^1$H NMR (CDCl$_3$) 0.88 (t, J=7.4 Hz, 3H, —(CH$_2$)$_{10}$CH$_3$), 1.20-1.65 (m, 18H, —CH$_2$—(CH$_2$)$_9$CH$_3$), 1.73-1.92 (m, 2H, C(3)-CH(OH)—CH$_2$—), 2.77 (d, J=4.1 Hz, 1H, C(3)-CH(OH)—), 5.39-5.43 (m, 1H, C(3)-CH(OH)—), 7.45 (s, 1H, C(6)-H), 9.64 (s, 1H, C(4)-OH), 9.91 (s, 1H, CHO), 11.62 (s, 1H, C(2)-OH); IR (KBr) 3445, 2926, 2839, 1637, 1308, 1232, 725 cm$^{-1}$.

In addition to this compound, methyl 5-chloro-2,4-dihydroxy-3-(1-hydroxydodecyl)benzoate (205-12) and 3-chloro-4,6-dihydroxy-5-(1-hydroxy-3,7-dimethyl-6-octenyl)-2-methylbenzaldehyde (220) were synthesized by the same reaction using corresponding aldehydes as the side chain precursors.

Example 23

Methyl 5-chloro-2,4-dihydroxy-3-(1-hydroxydodecyl)-benzoate (Compound No.: 205-12)

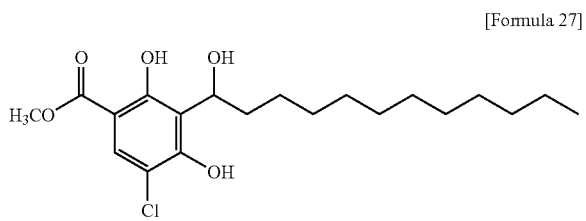

[Formula 27]

Methyl 5-Chloro-2,4-dihydroxy-3-(1-hydroxydodecyl)benzoate (205-12)

Mp 96-97° C.

$^1$H NMR (CDCl$_3$) 0.89 (t, J=7.0 Hz, 3H, —(CH$_2$)$_{10}$CH$_3$), 1.22-1.65 (m, 18H, —CH$_2$—(CH$_2$)$_9$CH$_3$), 1.73-1.92 (m, 2H, C(3)-CH(OH)—CH$_2$—), 2.78 (d, J=4.4 Hz, 1H, C(3)-CH(OH)—), 3.92 (s, 1H, COOCH$_3$), 5.38-5.42 (m, 1H, C(3)-CH(OH)—), 7.77 (s, 1H, C(6)-H), 9.52 (s, 1H, C(4)-OH), 11.18 (s, 1H, C(2)-OH); IR (KBr) 3474, 2918, 2860, 1674, 1348, 1250, 1209, 793 cm$^{-1}$.

Example 24

3-Chloro-4,6-dihydroxy-5-(1-hydrtoxy-3,7-dimethyl-6-octenyl)-2-methylbenzaldehyde (Compound No.: 220)

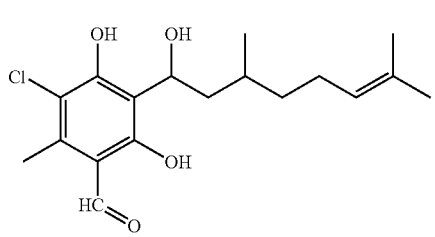

(Formula 28)

3-Chloro-4,6-dihydroxy-5-(1-hydroxy-3,7-dimethyl-6-octenyl)-2-methylbenz-aldehyde (220)

Colorless syrup $^1$H NMR (CDCl$_3$) 0.98 and 0.99 (two d, J=6.4 Hz, 3H, CHCH$_3$), 1.15-1.50 (m, 2H), 1.56-1.77 (m+s (1.595 and 1.602, CH$_3$)+s (1.67 and 1.68, CH$_3$), 8H), 1.84-2.09 (m, 3H), 2.57 (s, 3H, C(2)-CH$_3$), 3.23 (br s, 1H, C(3)-CH(OH)—), 5.05-5.11 (m, 1H, —CH═C(CH$_3$)$_2$), 5.40-5.45 (m, 1H, C(3)-CH(OH)—), 7.45 (s, 1H, C(6)-H), 9.87 and 9.99 (two br s, 1H, C(4)-OH), 10.08 and 10.09 (two s, 1H, CHO), 12.77 and 12.78 (two s, 1H, C(2)-OH).

Example 25

3-Chloro-4,6-dihydroxy-5-(1-hydroxy-3,7-dimethyl-6-octenyl)-2-methylbenzaldehyde (Compound No.: 203-12)

[Formula 29]

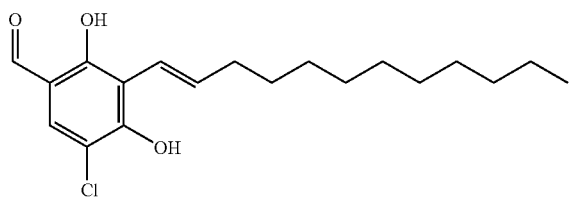

5-Chloro-3-(1-dodecenyl)-2,4-dihydroxybenzaldehyde (203-12)

5-Chloro-2,4-dihydroxy-3-(1-hydroxydodecyl) benzaldehyde (300 mg, 0.84 mmol) was stirred in acetic acid (2 ml) in the presence of 85% phosphoric acid (0.81 ml) at a reflux temperature for one hour. The reaction mixture was cooled to room temperature, added with a saturated sodium chloride solution (20 ml). After extractive workup with ethyl acetate, the crude product was purified by, silica gel column chromatography (hexane:ethyl acetate=10:1) to obtain 5-chloro-3-(1-dodecenyl)-2,4-dihydroxybenzaldehyde (pale yellow solid 238 mg, yield 84%)

Mp 84-85° C.

$^1$H NMR (CDCl$_3$) 0.88 (t, J=6.9 Hz, 3H, —(CH$_2$)$_7$C$\underline{H}_3$), 1.22-1.40 (m, 14H, —(C$\underline{H}_2$)$_7$CH$_3$), 1.43-1.55 (m, 2H, C(3)-CH=CH—CH$_2$—C$\underline{H}_2$—), 2.20-2.30 (m, 2H, C(3)-CH=CH—C$\underline{H}_2$—), 6.45 (s, 1H, C(4)-OH), 6.53 (d, J=16.3 Hz, 1H, C(3)-C$\underline{H}$=CH—CH$_2$—), 6.70 (dt, J=7.0, 16.3 Hz, C(3)-CH=C$\underline{H}$—CH$_2$—), 7.38 (s, 1H, C(6)-H), 9.67 (s, 1H, CHO), 11.88 (s, 1H, C(2)-OH); IR(KBr) 3100-3600, 2926, 2847, 1630, 1601, 1456, 1265, 1171, 1084, 974 cm$^{-1}$.

Elemental Analysis (Found): C, 67.06; H, 7.89; Cl, 10.30%. (Calcd. for C$_{19}$H$_{27}$ClO$_3$): C, 67.34; H, 8.03; Cl, 10.46%.

Example 26

3-Chloro-5-(3,7-dimethyl-1-octenyl)-4,6-dihydroxy-2-methylbenzaldehyde (Compound No.: dl-223)

[Formula 30]

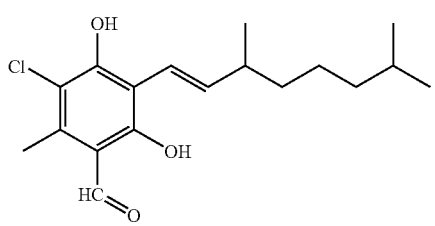

3-Chloro-5-(3,7-dimethyl-1-octenyl)-4,6-dihydroxy-2-methylbenzaldehyde (dl-223)

An ethanol solution (1.5 ml) of 3-chloro-5-(1-hydroxy-3,7-dimethyl-6-octenyl)-4,6-dihydroxy-2-methylbenzaldehyde (220) (196 mg, 0.57 mmol) was stirred at 0° C. in the presence of 5% Pd/C (50 mg) in a hydrogen atmosphere for 2 hours. After the catalyst was separated by filtration with the use of Celite, the filtrate was concentrated to obtain a crude product (188 mg). This crude product was purified by silica gel column chromatography (hexane:ethyl acetate=20:1) to obtain 3-chloro-5-(1-hydroxy-3,7-dimethyloctyl)-4,6-dihydroxy-2-methylbenzaldehyde (222, a diastereomeric mixture, red syrup 69 mg, crude yield 35%).

This crude product was subjected to the same dehydration reaction as in the synthesis of 5-chloro-3-(1-dodecenyl)-2,4-dihydroxybenzaldehyde (203-12) to synthesize the target 3-chloro-5-(3,7-dimethyl-1-octenyl)-4,6-dihydroxy-2-methylbenzaldehyde (223).

Yellow solid $^1$H NMR (CDCl$_3$) 0.86 (d, J=6.7 Hz, 6H, CH(C$\underline{H}_3$)$_2$), 1.09 (d, J=6.7 Hz, 3H, CH$_3$), 1.14-1.20 (m, 2H), 1.29-1.40 (m, 4H), 1.53 (sep, J=6.7 Hz, 1H, C$\underline{H}$(CH$_3$)$_2$), 2.28-2.35 (m, 1H), 2.62 (s, 3H, C(2)-CH$_3$), 6.48 (d, J=16.4 Hz, 1H, C(5)-C$\underline{H}$=CH—), 6.53 (dd, J=6.7, 16.4 Hz, 1H, C(5)-CH=C$\underline{H}$—), 6.60 (br s, 1H, C(4)-OH), 10.15 (s, 1H, CHO), 13.04 (s, 1H, C(2)-OH).

Example 27

3-Chloro-5-(3,7-dimethyloctyl)-4,6-dihydroxy-2-methylbenzaldehyde (tetrahydrocolletochlorin B) (Compound No.: dl-218)

[Formula 31]

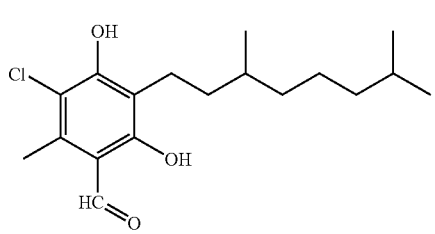

3-Chloro-5-(3,7-dimethyloctyl)-4,6-dihydroxy-2-methylbenzaldehyde (tetrahydrocolletochlorin B) (dl-218)

An ethanol solution (24.5 ml) of colletochlorin B (991 mg, 3.07 mmol) described in H. Saimoto et al., Bull. Chem. Soc. Jpn., 67, 1178 (1994) was stirred in the presence of 5% Pd/C (496 mg) at 0° C. in a hydrogen atmosphere for 4.5 hours. After the catalyst was separated by filtration with the use of Celite, the filtrate was concentrated to obtain a crude product (963 mg). This product was purified by silica gel column chromatography (hexane:diethyl ether=30:1) to obtain 3-chloro-4,6-dihydroxy-5-(3,7-dimethyloctyl)-2-methylbenzaldehyde (pale yellow solid 220 mg, yield 22%).

Mp 66-67° C.

$^1$H NMR (CDCl$_3$) 0.86 (d, J=6.7 Hz, 6H, CH(C$\underline{H}_3$)$_2$), 0.95 (d, J=6.7 Hz, 3H, CHC$\underline{H}_3$), 1.10-1.57 (m, 10H), 2.60 (s, 3H, C(2)-CH$_3$), 2.61-2.72 (m, 2H), 6.31 (br s, 1H, C(4)-OH), 10.14 (s, 1H, CHO), 12.64 (s, 1H, C(6)-OH); IR (KBr) 3100-

3500, 2951, 1614, 1460, 1421, 1244, 1132 cm$^{-1}$; MS m/z 328 (M+2, 3), 326 (M$^+$, 9), 202 (33), 200 (100).

Elemental Analysis (Found): C, 66.17; H, 8.50%. (Calcd. for $C_{18}H_{27}ClO_3$): C, 66.14; H, 8.33%.

In addition to this compound, the reduction of 3-chloro-4,6-dihydroxy-2-methyl-5-(1-nonenyl)benzaldehyde (200-9) to 3-chloro-4,6-dihydroxy-2-methyl-5-nonylbenzaldehyde (215-9) was conducted by the same reduction reaction.

Example 28

3-Chloro-4,6-dihydroxy-2-methyl-5-nonylbenzaldehyde (Compound No.: 215-9)

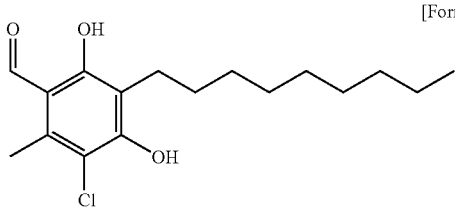

[Formula 32]

3-Chloro-4,6-dihydroxy-2-methyl-5-nonylbenzaldehyde (215-9)

Mp 89-90° C.
$^1$H NMR (CDCl$_3$) 0.88 (t, J=6.9 Hz, 3H, —(CH$_2$)$_7$-CH$_3$), 1.23-1.40 (m, 14H, —(CH$_2$)$_7$CH$_3$), 2.60 (s, 3H, C(2)-CH$_3$), 2.66 (d, J=7.7 Hz, 2H, C(3)-CH$_2$—), 6.30 (s, 1H, C(4)-OH), 10.14 (s, 1H, CHO), 12.65 (s, 1H, C(6)-OH); IR(KBr): 3100-3600, 2922, 2845, 1609, 1468, 1423, 1240, 1132 cm$^{-1}$; MS m/z 314 (M+2, 3), 312 (M$^+$, 9), 201 (39), 199 (100).

Example 29

3-Chloro-4,6-dihydroxy-2-methyl-5-[3-methyl-7-(tetrahydro-5,5-dimethyl-4-oxo-2-furanyl)octyl]-benzaldehyde (tetrahydroascofuranone) (Compound No.: 212)

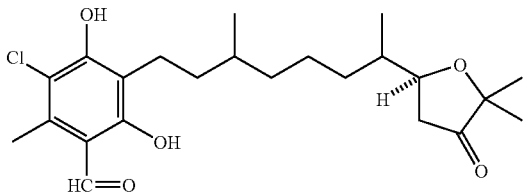

[Formula 33]

3-Chloro-4,6-dihydroxy-2-methyl-5-[3-methyl-7-(tetrahydro-5,5-dimethyl-4-oxo-2-furanyl)octyl]benzaldehyde (tetrahydroascofuranone, THAF) (212)

An ethanol (201 ml) solution of ascofuranone (1,058 mg, 2.52 mmlo) was stirred in the presence of 5% Pd/C (435 mg) in a hydrogen atmosphere at 0(C for three hours. After the catalyst was separated by filtration with the use of Celite, the filtrate was concentrated to obtain a crude product (1,178 mg). This product was purified by silica gel column chromatography (hexane:ethyl acetate=5:1) to obtain 3-chloro-4,6-dihydroxy-2-methyl-5-[3-methyl-7-(tetrahydro-5,5-dimethyl-4-oxo-2-furanyl)-octyl]benzaldehyde (a diastereomeric mixture, yellow syrup 262 mg, yield 25%).

$^1$H NMR (CDCl$_3$) 0.89 (d, J=6.8 Hz, 1.1H, CHCH$_3$), 0.955, 0.960, 0.98 (three d, J=6.5 Hz, 4.9H, CHCH$_3$), 1.05-1.83 (m+s (1.20, CH$_3$ of tetrahydrofuran moiety)+s (1.27, CH$_3$ of tetrahydrofuran moiety), 16H), 2.11-2.32 (m+s (2.17, C(2)-CH$_3$), 3.1H), 2.39-2.50 (m, 1H), 2.59-2.78 (m+s (2.60, C(2)-CH$_3$), 2.9H), 3.94-4.05 (m, 1H, C(2)-H of tetrahydrofuran moiety), 6.40 (br s, 1H, C(4)-OH), 10.14 (s, 1H, CHO), 12.65 (s, 1H, C(6)-OH); IR (neat) 3200-3600, 2934, 1751, 1626, 1460, 1420, 1246 cm$^{-1}$; MS m/z 426 (M+2, 1), 424 (M$^+$, 3), 201 (39), 199 (100).

Elemental Analysis (Found): C, 64.72; H, 7.68; Cl, 8.42%. (Calcd. for $C_{23}H_{33}ClO_3$): C, 65.01; H, 7.83; Cl, 8.34%.

Example 30

3-Chloro-6-hydroxy-4-methoxy-2-methyl-5-[(E,E)-3-methyl-7-(tetrahydro-5,5-dimethyl-4-oxo-2-furanyl)-2,6-octadienyl]benzaldehyde (4-O-Methylascofuranone) (Compound No.: 211)

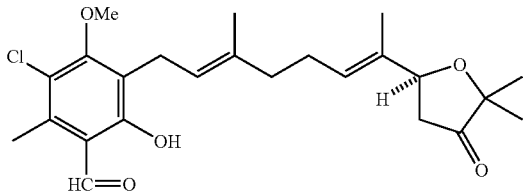

[Formula 34]

3-Chloro-6-hydroxy-4-methoxy-2-methyl-5-[(E,E)-3-methyl-7-(tetrahydro-5,5-dimethyl-4-oxo-2-furanyl) -2,6-octadienyl]benzaldehyde (4-O-Methylascofuranone) (211)

A dimethyl sulfate acetone solution (0.012 M, 20 ml) was added to ascofuranone (52 mg, 0.12 mmol) and stirred in the presence of potassium carbonate (16 mg, 0.11 mmol) at a reflux temperature for one hour. The reaction mixture was added with ethyl acetate and a saturated sodium chloride aqueous solution and extracted, and the extract was dried and concentrated to obtain a crude product (65 mg). This product was purified by silica gel thin-layer chromatography (hexane:ethyl acetate=5:1) to obtain 3-chloro?6-hydroxy-4-methoxy-2-methyl-5-[(E,E)-3-methyl-7-(tertrahydro-5,5-dimethyl-4-oxo-2-furanyl)-2,6-octadienyl]benzaldehyde (yellow-syrup 50 mg, yield 93%).

$^1$H NMR (CDCl$_3$) 1.22 (s, 3H, CH$_3$), 1.28 (s, 3H, CH$_3$), 1.62 (s, 3H, CH$_3$), 1.79 (s, 3H, CH$_3$), 2.00-2.07 (m, 2H), 2.09-2.20 (m, 2H), 2.35 (dd, J=10.2, 18.2 Hz, 1H, H—C(3)-H of tetrahydrofuran moiety), 2.41 (dd, J=6.4, 18.2 Hz, 1H, H—C(3)-H of tetrahydrofuran moiety), 2.64 (s, 3H, C(2)-CH$_3$), 3.38 (d, J=6.9 Hz, 2H, C(5)-CH$_2$—), 3.86 (s, 3H, OCH$_3$), 4.50 (dd, J=6.4, 10.2 Hz, 1H, C(2)-H of tetrahydrofuran moiety), 5.18 (t, J=6.3 Hz, 1H), 5.51 (t, J=6.9 Hz, 1H), 10.26 (s, 1H, CHO), 12.52 (s, 1H, C(6)-OH).

In addition to this compound, the conversion of 5-chloro-3-(1-dodecenyl)-2,4-dihydoxybenzaldehyde to 5-chloro-3-(1-dodecenyl)-2,4-dimethoxybenzaldehyde (210-12) was performed by the same methylation reaction.

Example 31

5-Chloro-3-(1-dodecenyl)-2,4-dimethoxybenzaldehyde (Compound No.: 210-12)

[Formula 35]

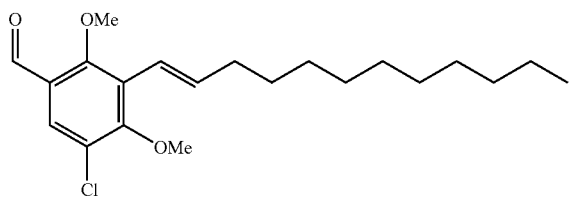

5-Chloro-3-(1-dodecenyl)-2,4-dimethoxybenzaldehyde (210-12)

Colorless syrup $^1$H NMR (CDCl$_3$) 0.88 (t, J=7.0 Hz, 3H, —(CH$_2$)$_7$C$\underline{H}_3$), 1.21-1.41 (m, 14H, —(C$\underline{H}_2$)$_7$CH$_3$), 1.47-1.54 (m, 2H, C(3)-CH=CH—CH$_2$—C$\underline{H}_2$—), 2.25-2.32 (m, 2H, C(3)-CH=CH—C$\underline{H}_2$—), 3.82 (s, 6H, OMe), 6.42 (d, J=16.2 Hz, 1H, C(3)-C$\underline{H}$=CH—CH$_2$—), 6.67 (dt, J=7.1, 16.2 Hz, C(3)-CH=C$\underline{H}$—CH$_2$—), 7.73 (s, 1H, C(6)-H), 10.27 (s, 1H, CHO).

Example 32

5-chloro-3-(1-dodecenyl)-2,4-dimethoxybenzaldehyde (Compound No.: 213)

[Formula 36]

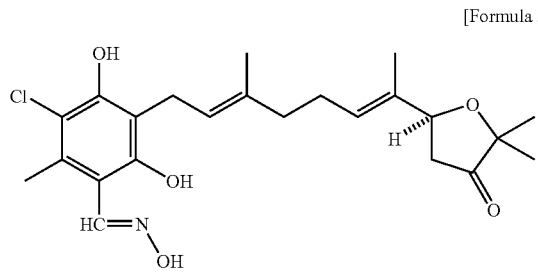

5-[(E,E)-7-(3-Chloro-2,6-dihydroxy-5-hydroxyiminomethyl-4-methylphenyl)-1,5-dimethyl-1,5-heptadienyl]-4,5-dihydro-2,2-dimethyl-3(2H)-furanone (Ascofuranone aldoxime) (213)

A hydroxylamine hydrochloride pyridine solution (0.22 M, 2.3 mmol) was added to ascofuranone (209 mg, 0.50 mmol) and stirred at room temperature for 1.5 hours. Furthermore, the hydroxylamine hydrochloride pyridine solution (0.22 M, 1.0 mmol) was added to the reaction mixture and stirred at 25° C. for two hours. After removing pyridine under reduced pressure, the resulting reaction solution was added with ethyl acetate and a saturated sodium chloride aqueous solution to perform extraction, and the extract was concentrated to obtain a crude product (270 mg), and this product was purified by silica gel column chromatography (hexane: ethyl acetate=3:1) to obtain 5-[(E,E)-7-(3-chloro-2,6-dihydroxy-5-hydroxyiminomethyl-4-methylphenyl)-1,5-dimethyl-1,5-heptadienyl]-4,5-dihydroxy-2,2-dimethyl-3(2H)-furanone (colorless solid 42 mg, yield 20%).

Mp 102-103° C.

$^1$H NMR (CDCl$_3$) 1.23 (s, 3H, CH$_3$), 1.29 (s, 3H, CH$_3$), 1.64 (s, 3H, CH$_3$), 1.78 (s, 3H, CH$_3$), 1.99-2.10 (m, 2H), 2.14-2.20 (m, 2H), 2.42 (s, 3H, Ar—CH$_3$), 2.43 (dd, J=9.4, 18.2 Hz, 1H, H—C(4)-$\underline{H}$), 2.46 (dd, J=6.8, 18.2 Hz, 1H, $\underline{H}$—C(4)-H), 3.41 (d, J=6.9 Hz, 2H, Ar—CH$_2$—), 4.52 (dd, J=6.8, 9.4 Hz, 1H, C(5)-H), 5.19 (t, J=6.5 Hz, 1H), 5.51 (t, J=6.9 Hz, 1H), 6.97 (s, 1H, C(2')-OH), 7.65 (s, 1H, N—OH), 8.53 (s, 1H, CH=N), 10.72 (s, 1H, C(6')-OH).

Elemental Analysis (Found): C, 63.08; H, 6.98; N, 3.06; Cl, 8.33%. (Calcd. for C$_{23}$H$_{30}$ClNO$_5$): C, 63.37; H, 6.94; N, 3.21; Cl, 8.13%.

Example 33

Antitrypanosoma Action (IC$_{50}$)

The respiration inhibition effect of the novel phenol derivatives on the cyanide resistant quinol enzyme of Trypanosoma was examined with the use of a recombinant enzyme. The results are shown in Table 1. AF means ascofuranone.

TABLE 1

| Antitrypanosoma Action | |
|---|---|
| Name of Substance | IC$_{50}$ (nM) |
| AF | 0.3 |
| 195-9 | 30 |
| 195-10 | 35 |
| 195-12 | 40 |
| 196-9 | 0.5 |
| 196-10 | 0.6 |
| 196-12 | 0.65 |
| 197 | 120 |
| 198 | 16 |
| 200-9 | 0.4 |
| 200-10 | 0.45 |
| 200-12 | 0.5 |
| 201-12 | 300 |
| 202-12 | 1.5 |
| 220 | 20 |
| 203-12 | 0.5 |
| dl-223 | 1.1 |
| dl-218 | 0.4 |
| 215-9 | 0.21 |
| 212 | 0.3 |
| 211 | 4.0 |
| 213 | 28.0 |

Example 34

Antitrypanosoma.Action (Effect of Addition of Glycerin)

With the use of a 96-well culture plate, each agent was adjusted to 10 mM with DMSO, and 5×10$^5$/ml of Trypanosma brucei brucei was added and cultured at 37° C. for 24 hours, and the minimum effective concentration was calculated.

The above described culture was conducted with the addition of 5 mM of glycerin under the same conditions as described above and observed. The results are shown in Table 2.

TABLE 2

Antitrypanosoma Action by Addition of Glycerin

| Name of substance | Minimum Effective Concentration (μM) | |
|---|---|---|
| | Absence of Glycerin | Presence of Glycerin |
| AF | 200 | 0.2 |
| 195-9 | 25 | 25 |
| 195-10 | 25 | 25 |
| 195-12 | 25 | 25 |
| 196-9 | 50 | 0.8 |
| 196-10 | 100 | 0.8 |
| 196-12 | 100 | 1.5 |
| 197 | 50 | 50 |
| 198 | 50 | 50 |
| 200-9 | 100 | 0.8 |
| 200-10 | 100 | 0.8 |
| 200-12 | 100 | 1.5 |

INDUSTRIAL APPLICABILITY

The compounds of the present invention have an excellent antitrypanosoma action and are very useful for preventing and treating the diseases caused by Trypanosoma.

The invention claimed is:

1. A compound represented by formula (I),

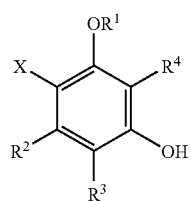

(I)

an optical isomer thereof, a pharmaceutically acceptable salt thereof, wherein

X is a hydrogen atom or a halogen atom;
$R^1$ is a hydrogen atom or —$(C_nH_{2n})$—R' (wherein n is an integer of 1 to 5; and R' is a hydrogen atom, a group COOR" or —COR'" of a substituent on any one of the n carbon atoms, wherein R" is a hydrogen atom or a $C_{1-4}$ alkyl group; and R'" is a pyridyl group, an amino group substituted with a $C_{1-4}$ alkyl group, a phenoxyalkyl group having a halogen atom on the carbon atoms of the benzene ring or a phenyl group having a $C_{1-4}$ alkoxy group or a $C_{1-4}$ alkoxycarbonyl group on the carbon atoms of the benzene ring);
$R^2$ is a hydrogen atom or a $C_{1-4}$ alkyl group;
$R^3$ is —CHO or —COOH; and
$R^4$ is —CH=CH—$(CH_2)_p$—$CH_3$ (wherein p is an integer of 1 to 12), —CH(OH)—$(CH_2)_q$—$CH_3$ (wherein q is an integer of 1 to 13), —CH(OH)—$CH_2$—$CH(CH_3)$—$(CH_2)_2$—CH=$C(CH_3)_2$, —CH=CH—$CH(CH_3)$—$(CH_2)_3$—$CH(CH_3)_2$, —$(CH_2)_2$—$CH(CH_3)$—$(CH_2)_3$—$CH(CH_3)_2$, or —$(CH_2)_8$—$CH_3$].

2. The compound of claim 1,
wherein
X is a hydrogen atom;
$R^1$ is a hydrogen atom;
$R^2$ is a $C_{1-4}$ alkyl group;
$R^3$ is —CHO; and
$R^4$ is —CH(OH)—$(CH_2)_q$—$CH_3$ (wherein q is an integer of 1 to 12), an optical isomer thereof, or pharmaceutically acceptable salt thereof.

3. The compound of claim 1,
wherein
X is a halogen atom;
$R^1$ is a hydrogen atom;
$R^2$ is a $C_{1-4}$ alkyl group;
$R^3$ is —CHO; and
$R^4$ is —CH(OH)—$(CH_2)_q$—$CH_3$ (wherein q is an integer of 1 to 12), an optical isomer thereof, or pharmaceutically acceptable salt thereof.

4. The compound of claim 1,
wherein
X is a hydrogen atom or a halogen atom;
$R^1$ is a hydrogen atom;
$R^2$ is a hydrogen atom or a $C_{1-4}$ alkyl group;
$R^3$ is —CHO; and
$R^4$ is —CH=CH—$(CH_2)_p$—$CH_3$ (wherein p is an integer of 1 to 12), an optical isomer thereof, or pharmaceutically acceptable salt thereof.

5. A compound selected from the following formulae:

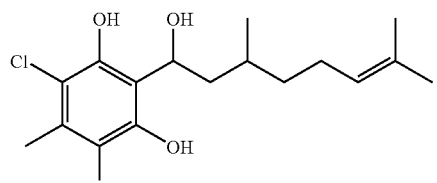

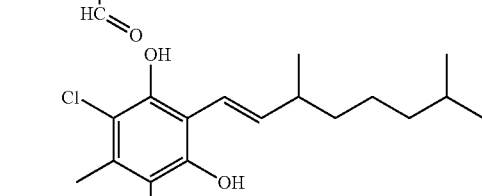

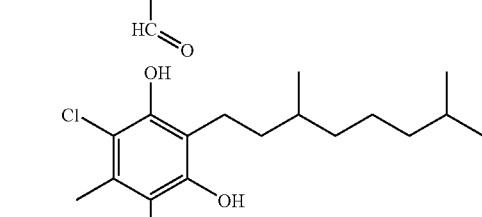

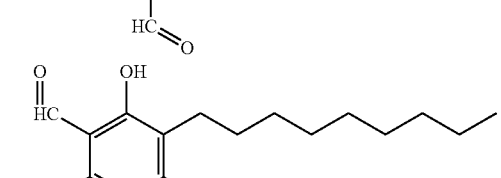

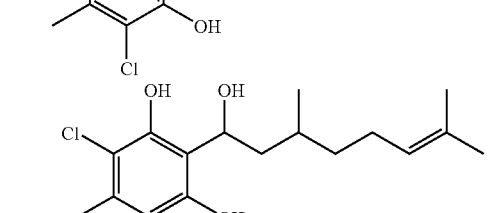

and

-continued

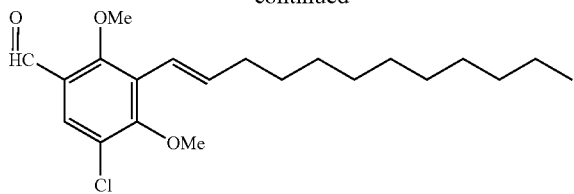

an optical isomer of any of them, or a pharmaceutically acceptable salt of any of them.

6. A pharmaceutical composition comprising a pharmaceutically acceptable carrier and a compound according to claim 1.

7. The pharmaceutical composition of claim 6, wherein
X is a hydrogen atom;
$R^1$ is a hydrogen atom;
$R^2$ is a $C_{1-4}$ alkyl group;
$R^3$ is —CHO; and
$R^4$ is —CH(OH)—(CH$_2$)$_q$—CH$_3$ (wherein q is an integer of 1 to 12.

8. The pharmaceutical composition of claim 6 wherein
X is a halogen atom;
$R^1$ is a hydrogen atom;
$R^2$ is a $C_{1-4}$ alkyl group;
$R^3$ is —CHO; and
$R^4$ is —CH(OH)—(CH$_2$)$_q$—CH$_3$, wherein q is an integer of 1 to 12.

9. The pharmaceutical composition of claim 6, wherein
X is a hydrogen atom or a halogen atom;
$R^1$ is a hydrogen atom;
$R^2$ is a hydrogen atom or a $C_{1-4}$ alkyl group;
$R^3$ is —CHO; and
$R^4$ is —CH=CH—(CH$_2$)$_p$—CH$_3$, wherein p is an integer of 1 to 12.

10. A pharmaceutical composition comprising a pharmaceutically acceptable carrier and a compound according to claim 5.

11. The pharmaceutical composition of claim 6 comprising glycerin.

12. The pharmaceutical composition of claim 7 comprising glycerin.

13. The pharmaceutical composition of claim 8 comprising glycerin.

14. The pharmaceutical composition of claim 9 comprising glycerin.

15. The pharmaceutical composition of claim 10 comprising glycerin.

* * * * *